United States Patent [19]

Goda et al.

[11] Patent Number: 5,101,049
[45] Date of Patent: Mar. 31, 1992

[54] NOVEL THIOPHENE DERIVATIVES AND METHODS FOR PRODUCING THE SAME

[75] Inventors: Hiroshi Goda; Masao Kawamura; Kunioki Kato; Makoto Sato, all of Hyogo, Japan

[73] Assignee: Seitetsu Kagaku Co., Ltd., Hyogo, Japan

[21] Appl. No.: 569,540

[22] Filed: Aug. 20, 1990

Related U.S. Application Data

[60] Continuation of Ser. No. 231,449, Aug. 12, 1988, abandoned, which is a division of Ser. No. 171,388, Mar. 21, 1988, Pat. No. 4,792,612, which is a continuation of Ser. No. 48,429, May 11, 1987, abandoned.

[30] Foreign Application Priority Data

| May 13, 1986 | [JP] | Japan | 61-110139 |
| May 13, 1986 | [JP] | Japan | 61-110140 |
| May 13, 1986 | [JP] | Japan | 61-110141 |
| Jan. 28, 1987 | [JP] | Japan | 62-019271 |
| Apr. 27, 1987 | [JP] | Japan | 62-104993 |

[51] Int. Cl.$^5$ .................. C07D 333/38; C07D 333/22
[52] U.S. Cl. ......................... 549/71; 549/70
[58] Field of Search ...................... 549/70, 71

[56] References Cited

U.S. PATENT DOCUMENTS

| 2,636,883 | 4/1953 | Byrns | 549/70 |
| 3,658,850 | 4/1972 | Davies | 549/70 |

FOREIGN PATENT DOCUMENTS

| 2518999 | 7/1983 | France | 549/70 |
| 1143374 | 7/1986 | Japan | 549/70 |

*Primary Examiner*—Alan Siegel
*Attorney, Agent, or Firm*—Wegner, Cantor, Mueller & Player

[57] ABSTRACT

Novel compounds, 2-($\alpha$-alkoxyimino)ethylthiophenes are susceptible to electrophilic substitution reactions, and the acetylation, nitration, sulfonation and halogenation of the compounds provide 5-acetyl-2-($\alpha$-alkoxyimino)ethylthiophenes, 5-nitro-2-($\alpha$-alkoxyimino)ethylthiophenes, 5-($\alpha$-alkoxyimino)ethyl-2-thiophenesulfonic acid and 5-halo-2-($\alpha$-alkoxyimino)ethylthiophenes, respectively.

The hydrolysis of 5-acetyl-2-($\alpha$-alkoxyimino)ethylthiophenes readily provides a known compound, 2,5-diacetylthiophene which is an important intermediate for the production of medicines, whereas the haloform reaction provides novel compounds, 5-($\alpha$-alkoxyimino)ethyl-2-thiophenecarboxylic acids, the hydrolysis of which compounds readily provides a known compound, 5-acetyl-2-thiophenecarboxylic acids, an important intermediate for the production of medicines.

The hydrolysis of 5-($\alpha$-alkoxyimino)ethyl-2-thiophenesulfonic acids and their salts provide novel 5-acetyl-2-thiophenesulfonic acid and its salts, respectively.

Novel compounds, 2-($\alpha$-alkoxyimino)ethylithiophenes are obtained either by O-alkylation of 2-acetylthiophene oxime or by directly reacting 2-acetylthiophene with an O-alkylhydroxylamine.

10 Claims, No Drawings

NOVEL THIOPHENE DERIVATIVES AND METHODS FOR PRODUCING THE SAME

This application is a continuation of U.S. application Ser. No. 231,449 filed Aug. 12, 1988, now abandoned which is a division of Ser. No. 171,388 filed Mar. 21, 1988, now U.S. Pat. No. 4,792,612, which is a continuation of Ser. No. 048,429 filed May 11, 1987, now abandoned.

This invention relates to novel thiophene derivatives and methods of producing the same.

2-($\alpha$-alkoxyimino)ethylthiophenes of the invention as novel compounds are widely utilizable as important intermediates for the production of medicines, agricultural chemicals or other chemicals. By way of example, the acetylation of 2-($\alpha$-alkoxyimino)ethylthiophenes gives 5-acetyl-2-($\alpha$-alkoxyimino)ethylthiophenes, which are also novel compounds, and the 5-acetyl-2-($\alpha$-alkoxyimino)ethylthiophenes, when being subjected to haloform reactions, provide 5-($\alpha$-alkoxyimino)ethyl-2-thiophenecarboxylic acids which are also novel compounds.

Further, the hydrolysis of 5-($\alpha$-alkoxyimino)ethyl-2-thiophenecarboxylic acids with an acid readily provide 5-acetyl-2-thiophenecarboxylic acid, a known compound. This thiophene derivative is an important intermediate for the production of, for example, a thienylthiazolylthioaminoalcohol derivative, as represented by the formula of

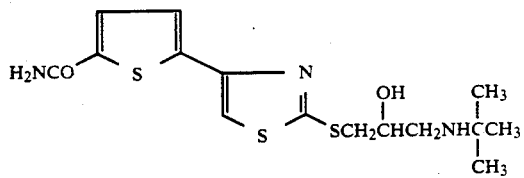

which is useful as medicates for irregular impulse, heart sickness or hypertension, as is disclosed in Japanese Patent Disclosures (Unexamined) Nos. 50-25562 and 50-76069. Meanwhile, the hydrolysis of aforesaid 5-acetyl-2-($\alpha$-alkoxyimino)ethylthiophenes with an acid readily gives known 2,5-diacetylthiophene, which is also an important intermediate for the production of various medicines and chemicals.

However, no method has heretofore been known which provides 5-acetyl-2-thiophenecarboxylic acid and 2,5-diacetylthiophene in industrially feasible manners and in high yields, although not a few methods for producing these thiophene derivatives have been hitherto known. For instance, it is already known that 5-acetyl-2-thiophenecarboxylic acid can be produced either by the hydrolysis of 5-cyano-2-acetylthiophene (J. Chem. Soc., 1937, 911), the oxidation of 2,5-diacetylthiophene (J. Amer. Chem. Soc., 69, 1012 (1947)), the acylation of thiophene-2-carboxylic acid esters (Ann. der Chem., 1, 1962), or the carboxylation of 2-methyl-2'-thienyl-1,3-dioxolane, but all of these methods are not industrially feasible from the viewpoint of raw materials needed, safety and controllability of the reactions.

Therefore, an improved method has been proposed, as disclosed in Japanese Patent Disclosures (Unexamined) Nos. 53-23963 and 53-141264, in which 2-thienylacetic acid is acetylated to provide 5-acetyl-2-thienylacetic acid or its esters, which are in turn oxidized, to provide 5-acetyl-2-thiophenecarboxylic acid. However, this method also has a disadvantage in that the reactions involved are not readily controllable. On the other hand, 2,5-diacetylthiophene can be produced by acetylation of 2-acetylthiophene, as is disclosed in J. Amer. Chem. Soc., 69, 1012 (1947), but the yields are very low.

The present inventors have made an extensive investigation of industrially advantageous methods for producing important thiophene derivatives such as, for example, 5-acetyl-2-thiophenecarboxylic acid and 2,5-diacetylthiophene, paying special attention to 2-acetylthiophene which is readily available as industrial raw materials. However, 2-acetylthiophene has a low electron density on the carbons on account of the electron attractive acetyl group so that especially 5-positioned carbon is resistant to electrophilic substitution reactions. This is the reason because the direct acetylation of 2-acetylthiophene provides 2,5-diacetylthiophene in very low yields, as described hereinbefore.

Then the inventors have made further investigations to increase the electron density on the carbons of the thiphene ring, and found out that the O-alkylation of 2-acetylthiophene oxime to convert the electron attractive acetyl group to electron donating $\alpha$-alkoxyiminoethyl groups increases the electron density on the carbons, especially 5-positioned carbon of the thiophene ring, and as results, the novel compounds, 2-($\alpha$-alkoxyimino)ethylthiophenes are readily acetylated by electrophilic substitution reactions, thereby to provide 5-acetylthiophene derivatives in high yields.

More specifically, 2-($\alpha$-alkoxyimino)ethylthiophenes are readily acetylated at the 5-position by, for example, acetic anhydride, to readily provide 5-acetyl-2-($\alpha$-alkoxyimino)ethylthiophenes, which readily provide known 2,5-diacetylthiophene by the hydrolysis with an acid. The oxidation of the thus introduced acetyl group of 5-acetyl-2-($\alpha$-alkoxyimino)ethylthiophenes to carboxyl group by use of haloform reactions readily provides 5-($\alpha$-alkoxyimino)ethylthiophenecarboxylic acids. Further the hydrolysis of these thiophenecarboxylic acids with an acid readily provides known 5-acetyl-2-thiophenecarboxylic acid. In this way, the novel compounds, 2-($\alpha$-alkoxyimino)ethylthiophenes of the invention are very useful as intermediates in synthetic organic industry.

The inventors have also found out that the 2-($\alpha$-alkoxyimino)ethylthiophenes are obtainable in higher yields by so-called one-pot reaction by directly reacting 2-acetylthiophene with an O-alkylhydroxylamine.

Turning to other electrophilic substitution reactions at thiophene derivatives, it is already known that the direct nitration of 2-acetylthiophene provides a mixture of 4-nitro-2-acetylthiophene and 5-nitro-2-acetylthiophene usually in molar ratios of the former to the latter of about 53 to 47, and 5-nitro-2-acetylthiophene can be separated from the 4-nitro isomer by silica gel chromatography, as disclosed in Australian Journal of Chemistry, 32, 2647 (1979). It is also already known that the nitration of 2-acetylthiophene oxime provides a mixture of 4-nitro-2-acetylthiophene oxime and 5-nitro-2-acetylthiophene oxime, and the recrystallization of the mixture from alcohols permits the separation of the 5-nitro isomer from the other, and further that 5-nitro-2-acetylthiophene oxime is hydrolyzed to provide 5-nitro-2-acetylthiophene, as disclosed in USSR 405878.

However, the first method produces 4-nitro-2-acetylthiophene as main reaction products, so that the separation of 5-nitro isomer is not easy, whereas the second method produces the objective product only in small yields.

On the other hand, neither 5-(α-alkoxyimino)ethyl-2-thiophenesulfonic acids, their salts, 5-acetyl-2-thiophenesulfonic acid, nor its salt have been hitherto known.

Oximes have been in general widely used for identification of organic compounds, however, the inventors have found out novel utilization of 2-acetylthiophene oxime as industrial raw materials for the production of a variety of novel thiophene derivatives useful as intermediates in synthetic organic industry.

It is, therefore, an object of the invention to provide novel thiophene derivatives and methods of producing the same by making use of 2-acetylthiophene oxime.

It is a specific object of the invention to provide novel 2-(α-alkoxyimino)ethylthiophenes and a method of producing the same.

It is still an object of the invention to provide novel 2-(α-alkoxyimino)ethyl-5-substituted thiophenes and a method of producing these compounds.

It is a specific object to provide 5-acetyl-2-(α-alkoxyimino)ethylthiophenes and 5-(α-alkoxyimino)ethyl-2-thiophenecarboxylic acids, both being novel compounds, and a method of producing these compounds.

It is also a specific object of the invention to provide a method of producing 2,5-diacetylthiophene and 5-acetyl-2-thiophenecarboxylic acid by making use of aforementioned 5-acetyl-2-(α-alkoxyimino)ethylthiophenes and 5-(α-alkoxyimino)ethyl-2-thiophenecarboxylic acids, respectively.

Still further it is an object of the invention to provide 2-(α-alkoxyimino)ethyl-5-nitrothiophenes, and a method of producing the same.

It is also a specific object of the invention to provide 2-(α-alkoxyimino)ethyl-5-halothiophenes and a method of producing the same.

It is still an object of the invention to provide 5-(α-alkoxyimino)ethyl-2-thiophenesulfonic acids and salts thereof, and a method of producing the same.

Still further it is an object of the invention to provide 5-acetyl-2-thiophenesulfonic acids and salts thereof, and a method of producing the same.

It is still an object of the invention to provide novel method of producing 5-nitro-2-acetylthiophene and 5-halo-2-acetylthiophenes.

At first, novel compounds, 2-(α-alkoxyimino)ethylthiophenes are provided according to the invention. The compounds have the general formula of

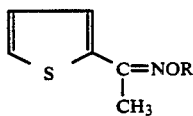

(I)

wherein R represents an alkyl having 1-4 carbons.

In the general formula (I), R represents a straight or branched alkyl having 1-4 carbons, and is exemplified by methyl, ethyl, n-propyl, isopropyl, n-butyl, sec.-butyl and tert.-butyl. Therefore, 2-(α-alkoxyimino)ethylthiophenes of the invention include 2-(α-methoxyimino)ethylthiophene, 2-(α-ethoxyimino)ethylthiophene, 2-(α-n-propoxyimino)ethylthiophene, 2-(α-isopropoxyimino)ethylthiophene, 2-(α-n-butoxyimino)ethylthiophene, 2-(α-sec.-butoxyimino)ethylthiophene, and 2-(α-tert.-butoxyimino)ethylthiophene.

As generally known, the oximes have two geometrical isomers, i.e., syn form and anti form, and the oximes of the invention also have syn form and anti form. In the syn form the alkoxy group lies at the same side as the thiophene ring, and in the anti form the alkoxy group lies at the opposite side to the thiophene ring. The oximes of the invention, therefore, may be either syn form or anti form, or a mixture of these isomers. The method of the invention which will be described hereinafter provides a mixture of the syn and anti forms of 2-(α-alkoxyimino)ethylthiophenes.

According to the invention, there is provided a method of producing 2-(α-alkoxyimino)ethylthiophenes having the general formula of

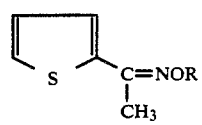

(I)

which comprises: O-alkylating 2-acetylthiophene oxime having the formula of

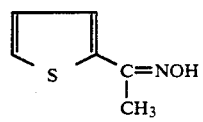

(II)

with an alkylating agent in the presence of a base.

2-Acetylthiophene oxime is a known compound, as is disclosed in Compt. rend., 234, 847 (1952), and may be produced by reacting 2-acetylthiophene with hydroxylamine in conventional manners in high yields.

By way of example, 2-acetylthiophene is reacted with hydroxylamine hydrochloride or sulfate in amounts of about 0.5-1.5 moles, preferably of 1.0-1.2 moles, per mole of 2-acetylthiophene in the presence of a base usually in the presence of solvents. The bases usable include, for example, hydroxides and carbonates of alkali metals or alkaline earth metals, however, sodium hydroxide is most commonly used. The amount of the bases used is not specifically limited, but it is usually not less than the equivalent to the hydroxylamine salts used.

Any solvent may be used if it is inactive to the reaction of the oxime formation and 2-acetylthiophene is soluble therein, however, preferred solvents are aqueous solutions of water miscible organic solvents such as lower aliphatic alcohols exemplified by methanol, ethanol and isopropanol; lower dialkyl ketones exemplified by acetone and methyl ethyl ketone; ethers exemplified by tetrahydrofurane and dioxane; acid imides exemplified by N,N-dimethylformamide and N,N-dimethylacetamide; or sulfoxides exemplified by dimethylsulfoxide.

The reaction is carried out usually at temperatures of about 50°-100° C., preferably of about 70°-90° C., usually for about 5-10 hours.

The oxime formation reaction is accelerated by adjusting the reaction mixture at a pH of about 2-6 with carboxylic acids. Namely, when the reaction mixture is adjusted at a pH of about 2-6 with carboxylic acids, 2-acetylthiophene oxime can be obtained substantially in the same yields in a reaction time shorter by about 1-2 hours than the reaction time needed under the same reaction conditions except for pH adjusting. As the carboxylic acids, for instance, lower aliphatic carboxylic acids having 1–4 carbons are usable, and acetic acid or propionic acid is most preferred.

After completion of the reaction, 2-acetylthiophene oxime may be separated by, for example, removing the solvents by distillation, or adding large quantities of water to the reaction mixture, followed by cooling the mixture and filtration of the resultant precipitates.

The 0-alkylation of 2-acetylthiophene oxime may be carried out according to conventional manners of 0-alkylation, and a variety of alkylating agents are usable in the invention. However, preferred examples of the alkylating agents usable in the invention are dialkylsulfuric acids and alkyl halides. The dialkylsulfuric acids usable in the invention have an alkyl of 1–4 carbons, and are exemplified by dimethylsulfuric acid, diethylsulfuric acid, di-n-propylsulfuric acid, diisopropylsulfuric acid, di-n-butylsulfuric acid, di-sec.-butylsulfuric acid and di-tert.-butylsulfuric acid. The alkyl halides usable in the invention also have an alkyl of 1–4 carbons and may be bromides or iodides. Therefore, alkyl halides usable in the invention include methyl bromide, methyl iodide, ethyl bromide, ethyl iodide, isopropyl bromide, isopropyl iodide, n-butyl bromide, sec.-butyl bromide, sec.-butyl iodide, tert.-butyl bromide or tert.-butyl iodide.

The alkylating agents are naturally selected depending upon the 0-alkylation needed by which 2-acetylthiophene oxime is 0-alkylated to the purpose.

In the 0-alkylation of 2-acetylthiophene oxime, the amount of the alkylating agents used is not specifically limited, but the amount is usually in the range of about 0.5–2 moles, preferably 1.0–1.2 moles, per mole of 2-acetylthiophene oxime. The use of too small amounts of the alkylating agents provides 2-(α-alkoxyimino)ethylthiophenes in only small yields, whereas the use of too excessive amounts are not attended by special advantage.

The 0-alkylation of 2-acetylthiophene oxime is carried out in the presence of a base, which includes, for example, hydroxides, hydrides, carbonates, hydrogencarbonates and alkoxides of alkali metals such as lithium, sodium or potassium, or of alkaline earth metals such as calcium. The bases preferably usable in the invention are exemplified by hydroxides such as lithium hydroxide, sodium hydroxide, potassium hydroxide or calcium hydroxide; hydrides such as lithium hydride, sodium hydride, potassium hydride or calcium hydride; carbonates such as sodium carbonate or potassium carbonate; hydrogencarbonates such as sodium hydrogencarbonate or potassium hydrogencarbonate; and alkoxides such as sodium alkoxide or potassium alkoxide. However, the alkali metal hydroxides, alkali metal hydrides and alkali metal alkoxides are preferred since the use of these bases provides especially high yields of 2-(α-alkoxyimino)ethylthiophenes.

However, tertiary amines are also usable as bases, if necessary, and the tertiary amines usable include aliphatic, aromatic and alicyclic tertiary amines, and nitrogen containing six membered heteroaromatic compounds. These tertiary amines include, for example, triethylamine, dimethylaniline and pyridine.

The amount of the bases used are also not specifically limited, but it is usually in the range of about 0.8–2 moles, preferably in the range of about 1.0–1.2 moles, per mole of 2-acetylthiophene oxime used. Similarly to the case of the alkylating agents, the use of too small amounts of the bases provides 2-(α-alkoxyimino)ethylthiophenes only in small yields, whereas the use of too large amounts are not attended by special advantage.

The 0-alkylation of 2-acetylthiophene oxime is carried out usually in solvents. The solvents used are not specifically limited provided that they are inactive to the reaction, and 2-acetylthiophene oxime is soluble therein, but preferred solvents are water, lower aliphatic alcohols such as methanol, ethanol or isopropanol; lower aliphatic ketones such as acetone, methyl ethyl ketone or methyl isobutyl ketone; aliphatic or alicyclic ethers such as diethyl ether, tetrahydrofurane or dioxane; halogenated hydrocarbons such as dichloroethane, chloroform, carbon tetrachloride or chlorobenzene; aromatic hydrocarbons such as benzene, toluene or xylene; open chain carboxylic acid amides such as N,N-dimethylformamide or N,N-dimethylacetamide; sulfoxides such as dimethylsulfoxide; and mixtures of two or more of these. Among these solvents, however, N,N-dimethylformamide or its aqueous solution, i.e., hydrous N,N-dimethylformamide is particularly preferred since these provides 2-(α-alkoxyimino)ethylthiophenes in higher yields than the other solvents.

The reaction temperature of 0-alkylating reaction of 2-acetylthiophene oxime is usually in the range of from about −10° C. to about 50° C., preferably from about 0° C. to about 35° C., and most preferably from about 5° C. to about 20° C. When the reaction temperature is higher than about 50° C., undesired side reactions take place to decrease the yields of 2-(α-alkoxyimino)ethylthiophenes, while when the reaction temperature is lower than about −10° C., the reaction proceeds too slowly from the viewpoint of the industrial production of 2-(α-alkoxyimino)ethylthiophenes.

The reaction time may be within several hours, and usually the reaction completes within about 1–2 hours.

Various methods may be adopted to isolate 2-(α-alkoxyimino)ethylthiophenes from the resultant reaction mixture. By way of example only, after the completion of the reaction, the reaction mixture is extracted with, for example, chloroform, the extract is washed with water, chloroform is distilled off, and then the residue is vacuum distilled, to provide 2-(α-alkoxyimino)ethylthiophenes usually as liquids. The direct vacuum distillation of the reaction mixture also permits the isolation of 2-(α-alkoxyimino)ethylthiophenes.

There is further provided a method of producing 2-(α-alkoxyimino)ethylthiophenes having the aforementioned general formula (I), which comprises: reacting 2-acetylthiophene with an 0-alkylhydroxylamine having the general formula of RONH2 wherein R represents an alkyl having 1–4 carbons.

The 0-alkylhydroxylamines usable in the invention include 0-methylhydroxylamine, 0-ethylhydroxylamine, 0-n-propylhydroxylamine, 0-isopropylhydroxylamine, 0-n-butylhydroxylamine, 0-sec.-butylhydroxylamine and 0-tert.-butylhydroxylamine. The 0-alkylhydroxylamines used are selected in accordance with the 0-alkyloxime formation reaction needed by which 2-acetylthiophene is 0-alkoxyimidated to the purpose.

In the 0-alkyloxime formation reaction of 2-acetylthiophene, the amount of the 0-alkylhydroxylamines used is not specifically limited, but is usually in the range of about 0.5–2 moles, preferably about 1.0–1.5 moles, per mole of 2-acetylthiophene used. The use of too small amounts of the 0-alkylhydroxylamines provides 2-(α- alkoxyimino)ethylthiophenes only in small yields, while the use of too large amounts are not attended by special advantage.

Since the O-alkylhydroxylamines are available usually as salts of mineral acids, such as hydrochlorides or sulfonates, the reaction is carried out in the presence of a base to make the salts free O-alkylhydroxylamines.

The bases usable include, for example, hydroxides, hydrides, carbonates, hydrogencarbonates and alkoxides of alkali metals such as lithium, sodium or potassium, or of alkaline earth metals such as calcium. The bases preferably usable in the invention are exemplified by hydroxides such as lithium hydroxide, sodium hydroxide, potassium hydroxide or calcium hydroxide; hydrides such as lithium hydride, sodium hydride, potassium hydride or calcium hydride; carbonates such as sodium carbonate or potassium carbonate; hydrogencarbonates such as sodium hydrogencarbonate or potassium hydrogencarbonate; and alkoxides such as lithium alkoxide, sodium alkoxide or potassium alkoxide. However, the alkali metal hydroxides and alkali metal carbonates are preferred since the use of these bases provides especially high yields of 2-($\alpha$-alkoxyimino)ethylthiophenes. Sodium hydroxide or sodium carbonate is most preferred.

The amount of the bases used is usually in the range of about 0.8–2 moles, preferably of about 1.0–1.2 moles, per mole of the O-alkylhydroxylamines used. The use of too small amounts of the bases provides 2-($\alpha$-alkoxyimino)ethylthiophenes only in small yields, while the use of too large amounts are not attended by special advantage.

The O-alkyloxime formation of 2-acetylthiophene is carried out usually in solvents. The solvents used are not specifically limited provided that they are inactive to the reaction, and 2-acetylthiophene is soluble therein, but preferred solvents are water, lower aliphatic alcohols such as methanol, ethanol or isopropanol; lower aliphatic ketones such as acetone or methyl ethyl ketone; aliphatic or alicyclic ethers such as diethyl ether, tetrahydrofurane or dioxane; open chain carboxylic acid amides such as N,N-dimethylformamide or N,N-dimethylacetamide; sulfoxides such as dimethylsulfoxide; and mixtures of two or more of these.

The reaction temperature of O-alkyloxime formation reaction of 2-acetylthiophene is usually in the range of about 40°–120° C., preferably of about 60°–90° C. When the reaction temperature is higher than about 120° C., undesired side reactions take place to decrease the yields of 2-($\alpha$-alkoxyimino)ethylthiophenes, while when the reaction temperature is lower than about 40° C., the reaction proceeds too slowly from the viewpoint of the industrial production of 2-($\alpha$-alkoxyimino)ethylthiophenes.

The reaction time is not specifically limited, but it is usually in the range of about 3–10 hours.

Similarly to the production of 2-acetylthiophene oxime, the O-alkyloxime formation of 2-acetylthiophene is accelerated by adjusting the reaction mixture at a pH of about 2–6 with carboxylic acids. 2-($\alpha$-Alkoxyimino)ethylthiophenes can be obtained substantially in the same yields in a reaction time shortened by about 1–2 hours than the reaction time needed under the same reaction conditions except for pH adjusting at about 2–6 in the presence of carboxylic acids. As the carboxylic acids, for instance, lower aliphatic carboxylic acids having 1–4 carbons are usable, and acetic acid or propionic acid is most preferred.

Various methods may be adopted to isolate 2-($\alpha$-alkoxyimino)ethylthiophenes from the resultant reaction mixture. By way of example, after completion of the reaction, 2-($\alpha$-alkoxyimino)ethylthiophenes may be separated by extracting the reaction mixture with chloroform, the extract is washed with water, chloroform is removed by distillation therefrom, and the residue is distilled in vacuo, to provide 2-($\alpha$-alkoxyimino)ethylthiophenes usually as liquid in very high purities and in very high yields. The thus obtained 2-($\alpha$-alkoxyimino)ethylthiophenes are so pure that they can be satisfactorily used as they are without further purification, for instance, for the production of 5-acetyl-2-($\alpha$-alkoxyimino)ethylthiophenes. However, the 2-($\alpha$-alkoxyimino)ethylthiophenes may be further purified, if necessary, by distillation in vacuo. Highly pure 2-($\alpha$-alkoxyimino)ethylthiophenes may also be separated by the direct distillation of the reaction product under reduced pressures.

According to the invention, there are further provided novel 2-($\alpha$-alkoxyimino)ethylthiophene derivatives having the general formula of

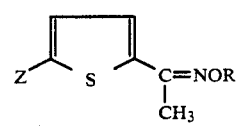

(III)

wherein R represents an alkyl having 1–4 carbons, and Z represents acetyl or carboxyl. More specifically, the invention provides novel compounds, 5-acetyl-2-($\alpha$-alkoxyimino)ethylthiophenes represented by the general formula of

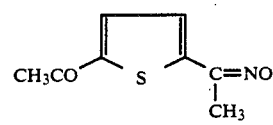

(IV)

wherein R represents an alkyl having 1–4 carbons; and novel compounds, 5-($\alpha$-alkoxyimino)ethyl-2-thiophenecarboxylic acids represented by the general formula of

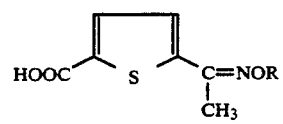

(V)

wherein R represents an alkyl having 1–4 carbons. In both of the acetylated compounds (IV) and carboxylic acid derivatives (V), R represents a straight or branched alkyl having 1–4 carbons, and is exemplified by methyl, ethyl, n-propyl, isopropyl, n-butyl, sec.-butyl and tert.-butyl.

Therefore, 5-acetyl-2-($\alpha$-alkoxyimino)ethylthiophenes of the invention include 5-acetyl-2-($\alpha$-methoxyimino)ethylthiophene, 5-acetyl-2-($\alpha$-ethoxyimino)ethylthiophene, 5-acetyl-2-($\alpha$-n-propoxyimino)ethylthiophene, 5-acetyl-2-($\alpha$-isopropoxyimino)ethylthiophene, 5-acetyl-2-($\alpha$-n-butoxyimino)ethylthiophene, and 5-acetyl-2-($\alpha$-tert.-butoxyimino)ethylthiophene.

Similarly, 5-($\alpha$-alkoxyimino)ethyl-2-thiophenecarboxylic acids of the invention include, for instance, 5-(α-methoxyimino)ethyl-2-thiophenecarboxylic acid, 5-(α-ethoxyimino)ethyl-2-thiophenecarboxylic acid, 5-(α-n-propoxyimino)ethyl-2-thiophenecarboxylic acid, 5-(α-isopropoxyimino)ethyl-2-thiophenecarboxylic acid, 5-(α-n-butoxyimino)ethyl-2-thiophenecarboxylic acid, and 5-(α-tert.-butoxyimino)ethyl-2-thiophenecarboxylic acid.

According to the invention, a method of producing of 5-acetyl-2-(α-alkoxyimino)ethylthiophenes is provided, which comprises: acetylating 2-(α-alkoxyimino)ethylthiophenes with an acetylating agent in the presence of a catalyst. Acetic anhydride or acetyl halides such as acetyl chloride are preferably used as the acetylating agents, and Lewis acids such as aluminum chloride, zinc chloride or ferric chloride are preferably used as the catalysts. When acetic anhydride is used as an acetylating agent, acid catalysts are also usable such as sulfuric acid, polyphosphoric acid or perchloric acid, and polyphosphoric acid is most preferred.

The amount of the acetylating agents used is not specifically limited, but it is usually in the range of about 1-10 moles, preferably 1.0-5 moles, per mole of 2-(α-alkoxyimino)ethylthiophenes used.

The acetylation reaction of 2-(α-alkoxyimino)ethylthiophenes may be carried out in the absence of solvents, but it is preferred that the reaction is carried out in the presence of solvents, such as acetic anhydride or halogenated hydrocarbons such as dichloromethane, 1,2-dichloroethane, chloroform or carbon tetrachloride. Further the reaction is carried out normally at temperatures of about 40°-120° C., preferably of about 50°-110° C., for about 1-20 hours, preferably for about 5-12 hours. When the reaction temperature is higher than about 120° C., undesired side reactions take place, whereas when the reaction temperature is lower than about 40° C., the reaction proceeds too slowly.

Further according to the invention, there is provided a method of producing 5-(α-alkoxyimino)ethyl-2-thiophenecarboxylic acids, which comprises: oxidatively decomposing 5-acetyl-2-(α-alkoxyimino)ethylthiophenes with alkali metal or alkaline earth metal hypohalites. Namely, 5-(α-alkoxyimino)ethyl-2-thiophenecarboxylic acids are produced by subjecting 5-acetyl-2-(α-alkoxyimino)ethylthiophenes to haloform reactions.

As the hypohalites usable in the haloform reaction, there are mentioned, for example, sodium hypochlorite, sodium hypobromite, potassium hypochlorite, potassium hypobromite and calcium hypochlorite. The hypochlorites are used in the reaction in amounts of about 2-5 moles, preferably of about 3-4 moles, per mole of 5-acetyl-2-(α-alkoxyimino)ethylthiophenes used. The reaction is carried out in solvents such as water or aqueous solutions of water miscible organic solvents, for instance, aliphatic lower alcohols including methanol or ethanol. The reaction temperature is usually in the range of about 20°-100° C., preferably in the range of about 40°-70° C. When the reaction temperature is higher than about 100° C., undesired side reactions take place, whereas when the reaction temperature is lower than about 20° C., the reaction proceeds too slowly.

The haloform reactions proceed rapidly and completes usually within a few hours. In typical cases, the reaction may be carried out for about 0.5-1.5 hours.

As still important aspects of the invention, there are provided novel methods for producing 2,5-diacetylthiophene and 5-acetyl-2-thiophenecarboxylic acid by use of aforementioned 5-acetyl-2-(α-alkoxyimino)ethylthiophenes and 5-(α-alkoxyimino)ethyl-2-thiophenecarboxylic acids, respectively.

The method of producing 2,5-diacetylthiophene and 5-acetyl-2-thiophenecarboxylic acid according to the invention comprises: hydrolyzing 2-(α-alkoxyimino)ethylthiophene derivatives having the general formula of

(III)

wherein R represents an alkyl having 1-4 carbons, and Z represents a group selected from the group consisting of acetyl and carboxyl in the presence of an acid, whereby to provide a 2-acetylthiphene derivative having the general formula of

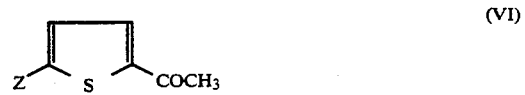

(VI)

Therefore, more specifically, there is provided a novel method of producing 2,5-diacetylthiophene, which comprises: hydrolyzing 5-acetyl-2-(α-alkoxyimino)ethylthiophenes having the general formula of

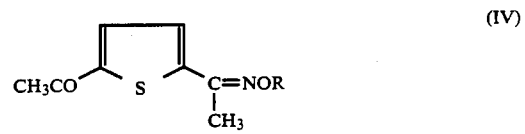

(IV)

wherein R represents an alkyl having 1-4 carbons in the presence of an acid.

There is further provided a method of producing 5-acetyl-2-thiophenecarboxylic acid, which comprises: hydrolyzing 5-(α-alkoxyimino)ethyl-2-thiophenecarboxylic acids having the general formula of

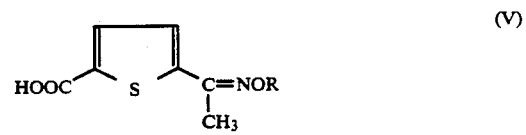

(V)

wherein R represents an alkyl having 1-4 carbons in the presence of an acid.

Preferred examples of 5-acetyl-2-(α-alkoxyimino)ethylthiophenes usable in the method of the invention include, for instance, 5-acetyl-2-(α-methoxyimino)ethylthiophene, 5-acetyl-2-(α-ethoxyimino)ethylthiophene, 5-acetyl-2-(α-n-propoxyimino)ethylthiophene, 5-acetyl-2-(α-isopropoxyimino)ethylthiophene, 5-acetyl-2-(α-n-butoxyimino)ethylthiophene and 5-acetyl-2-(α-tert.-butoxyimino)ethylthiophene.

Preferred examples of 5-(α-alkoxyimino)ethyl-2-thiophenecarboxylic acids usable in the method of the invention include, for instance, 5-(α-methoxyimino)ethyl-2-thiophenecarboxylic acid, 5-(α-ethoxyimino)ethyl-2-thiophenecarboxylic acid, 5-(α-n-propoxyimino)ethyl-2-thiophenecarboxylic acid, 5-(α-isopropoxyimino)ethyl-2-thiophenecarboxylic acid, 5-(α-n-butoxyimino)ethyl-2-thiophenecarboxylic acid and 5-(α-tert.-butoxyimino)ethyl-2-thiophenecarboxylic acid.

In the acid hydrolysis either of 5-acetyl-2-(α-alkoxyimino)ethylthiophenes or of 5-(α-alkoxyimino)ethyl-2-thiophenencarboxylic acids, the use of inorganic acids are preferred, such as hydrochloric acid, sulfuric acid or phosphoric acid, however, organic acids are also usable when necessary, such as p-toluenesulfonic acid and the like. The acids are used usually in amounts of about 5-50 moles per mole of the starting material, i.e., 5-acetyl-2-(α-alkoxyimino)ethylthiophenes or of 5-(α-alkoxyimino)ethyl-2-thiophenecarboxylic acids used. In particular, the use of the acids in amounts of about 10-30 moles per mole of the starting material is preferred since the hydrolysis reaction completes within a shorter period of time. From another point of view, hydrochloric acid is preferred since the reaction produces the objective product in higher yields.

The hydrolysis reaction is carried out usually in solvents such as water or an aqueous solution of water miscible organic solvents, which are exemplified by, for example, methanol, ethanol or acetone, for, for instance, about 2-12 hours, preferably for about 3-10 hours. The reaction temperature is usually in the range of about 20°-80° C., preferably in the range of about 40°-70° C., since when the reaction temperature is too high, undesired side reactions take place, while when the reaction temperature is too low, the reaction proceeds very slowly.

The invention further provides novel thiophene compounds, that is, 5-nitro-2-(α-alkoxyimino)ethylthiophenes, 5-halo-2-(α-alkoxyimino)ethylthiophenes, and 5-(α-alkoxyimino)ethyl-2-thiophenesulfonic acids, and methods of producing the same as well.

The invention still further provides novel methods of producing 5-nitro-2-acetythiophene, 5-halo-2-acetylthiophenes, and 5-acetyl-2-thiophenesulfonic acid, but also provides 5-acetyl-2-thiophenesulfonic acid as a novel compound.

The novel thiophene derivatives of the invention are represented by the general formula of

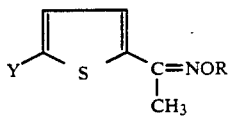

(VII)

wherein R represents an alkyl having 1-4 carbons, and Y represents a group selected from the group consisting of nitro, halogen, sulfonic acid group and alkali metal sulfonate group.

In the general formula (VII), R represents a straight or branched alkyl having 1-4 carbons, and is exemplified by methyl, ethyl, n-propyl, isopropyl, n-butyl, sec.-butyl and tert.-butyl. Therefore, 5-nitro-2-(α-alkoxyimino)ethylthiophenes of the invention include 5-nitro-2-(α-methoxyimino)ethylthiophene, 5-nitro-2-(α-ethoxyimino)ethylthiophene, 5-nitro-2-(α-n-propoxyimino)ethylthiophene, 5-nitro-2-(α-isopropoxyimino)ethylthiophene, 5-nitro-2-(α-n-butoxyimino)ethylthiophene, and 5-nitro-2-(α-tert.-butoxyimino)ethylthiophene.

5-Halo-2-(α-alkoxyimino)ethylthiophenes of the invention include chlorides, bromides and iodides, however, the chlorides and bromides are especially useful as intermediates for the production of thiophene derivatives. These chlorides and bromides include, for instance, 5-bromo- or chloro-2-(α-methoxyimino)ethylthiophene, 5-bromo- or chloro-2-(α-ethoxyimino)ethylthiophene, 5-bromo- or chloro-2-(α-n-propoxyimino)ethylthiophene, 5-bromo- or chloro-2-(α-isopropoxyimino)ethylthiophene, 5-bromo- or chloro-2-(α-n-butoxyimino)ethylthiophene, and 5-bromo- or chloro-2-(α-tert.-butoxyimino)ethylthiophene.

5-(α-Alkoxyimino)ethyl-2-thiophenesulfonic acids and alkali metal salts thereof of the invention include, for example, 5-(α-methoxyimino)ethyl-2-thiophenesulfonic acid and alkali metal salts thereof, 5-(α-ethoxyimino)ethyl-2-thiophenesulfonic acid and alkali metal salts thereof, 5-(α-n-propoxyimino)ethyl-2-thiophenesulfonic acid and alkali metal salts thereof, 5-(α-isopropoxyimino)ethyl-2-thiophenesulfonic acid and alkali metal salts thereof, 5-(α-n-butoxyimino)ethyl-2-thiophenesulfonic acid and alkali metal salts thereof, and 5-(α-tert.-butoxyimino)ethyl-2-thiophenesulfonic acid and alkali metal salts thereof.

Since the free 5-(α-alkoxyimino)ethyl-2-thiophenesulfonic acids are rather unstable, although it can be isolated, the sulfonic acids are usually isolated and used as alkali metal salts. The alkali metal sulfonates of the invention are usually provided as sodium salts or potassium salts, the former being more useful than the latter from the industrial point of view.

Methods for producing 5-nitro-2-(α-alkoxyimino)ethylthiophenes, 5-(α-alkoxyimino)ethyl-2-thiophenesulfonic acids and alkali metal salts thereof are now described.

5-Nitro-2-(α-alkoxyimino)ethylthiophenes are obtained by nitration of 2-(α-alkoxyimino)ethylthiophenes with a nitrating agent. Mixed acids, i.e., mixtures of sulfuric acid and nitric acid, or nitric acid in cojunction with acetic anhydride which produces acetyl nitrate as a nitrating agent, is preferably used as a nitrating agent. The amount of the nitrating agents used is not specifically limited, but it is usually in the amount of about 1-3 moles, preferably in the amount of about 1.5-2 moles, per mole of 2-(α-alkoxyimino)ethylthiophenes used. The use of too small amounts of the nitrating agents provides the objective nitrated compounds only in very small yields, whereas the use of too large amounts of the nitrating agents is attended by no special advantage.

The nitration is carried out at temperatures usually in the range of from about −10° C. to about 15° C., preferably in the range of from about −5° C. to about 10° C. When the reaction temperature is too high, undesired side reactions take place, while when the reaction temperature is too low, the reaction proceeds very slowly.

The nitration reaction time is usually within 10 hours, for example, in the range of about 1-6 hours, although being not limited thereto.

5-Halo-2-(α-alkoxyimino)ethylthiophenes are obtained by halogenation of 2-(α-alkoxyimino)ethylthiophenes with halogens in the presence of a catalyst. In the halogenation, heavy metals such as iron, or Lewis acids such as aluminum chloride, are preferably used as the catalyst. Chlorine or bromine is preferred as halogenating agents in the invention, and the halogens are used usually in amounts of about 1.0-1.5 moles, preferably of about 1.0-1.2 moles, per mole of 2-(α-alkoxyimino)ethylthiophenes used. The use of too small amounts of halogens results in the production of the objective halogenated thiophene derivative in very small yields, whereas the use of too large amounts of halogens is not attended by special advantage. Sulfuryl chloride is also usable as a chlorinating agent to produce 5-chloro-2-(α-alkoxyimino)ethylthiophenes. The reaction may be carried out in conventional manners, if necessary, in the presence of peroxides.

The halogenation of 2-(α-alkoxyimino)ethylthiophenes is carried out usually in organic solvents, preferably halogenated hydrocarbons, such as chloroform, dichloroethane, or dichloromethane at temperatures of about 20°-80° C., preferably of about 40°-60° C. When the reaction temperature is too high, undesired side reactions take place, and when the reaction temperature is too low, the reaction proceeds very slowly.

The reaction may be carried out for several hours to about 20 hours, but is usually in the range of about 5-10 hours.

5-(α-Alkoxyimino)ethyl-2-thiophenesulfonic acids are obtained by sulfonation of 2-(α-alkoxyimino)ethylthiophenes with a sulfonating agent. After the reaction, the neutralization of the resultant reaction mixture with, for example, alkali metal hydroxides, provides alkali metal salts of 5-(α-alkoxyimino)ethyl-2-thiophenesulfonic acids. The sulfonating agents usable include fuming sulfuric acid and chlorosulfuric acid. These sulfonating agents are used in amounts of about 1-10 moles, preferably of about 1.5-5 moles per mole of 2-(α-alkoxyimino)ethylthiophenes used. The use of too small amounts of sulfonating agents results in the production of the objective compound in very small yields, whereas the use of too large amounts of agents is not attended by special advantage.

The sulfonation reaction may be carried out either in the presence or absence of solvents, however, the use of solvents is preferred. Halogenated hydrocarbons such as dichloroethane, chloroform or dichloromethane, or carbon disulfide are preferably usable as solvents. The sulfonation is carried out usually at temperatures of about 10°-60° C., preferably of about 20°-40° C., although being not limited thereto, since when the reaction temperature is too high, undesired side reactions take place, while when the reaction temperature is too low, the reaction proceeds very slowly.

The reaction time may be usually within about 10 hours, and preferably in the range of about 1-5 hours, although being not limited thereto.

According to the invention, the hydrolysis of 5-nitro-2-(α-alkoxyimino)ethylthiophenes, 5-halo-2-(α-alkoxyiminoethylthiophenes, and 5-(α-alkoxyimino)ethyl-2-thiophenesulfonic acids (or their alkali metal salts) with an acid provides 5-nitro-2-acetylthiophene, 5-halo-2-acetylthiophenes, 5-acetyl-2-thiophenesulfonic acid (or their alkali metal salts), in high yields, respectively. The hydrolysis is carried out usually with inorganic acids such as hydrochloric acid, sulfuric acid or phosphoric acid usually in amounts of 5-50 moles per mole of the starting compounds used. However, 10-30 moles of the acids per mole of the starting compounds are preferably used so that the reaction completes in relatively short period of time.

However, the hydrolysis may be carried out in water in the presence of organic acids such as p-toluenesulfonic acid usually in amounts of 5-50 moles, preferably 10-30 moles, per mole of the starting compounds used.

The reaction temperature of the hydrolysis depends upon the starting compounds used, however, it is usually in the range of about 20°-80° C., preferably in the range of about 40°-70° C., since when the reaction temperature is too high, undesired side reactions take place, while when the reaction temperature is too low, the reaction proceeds very slowly, resulting in small yields of the objective products in feasible reaction time. The reaction time may be not more than 20 hours, and usually the reaction is carried out for about 3-10 hours.

The invention will be more easily understood with reference to the following examples, which however are intended to illustrate the invention only and are not to be construed as limiting to the scope of the invention.

REFERENCE

Synthesis of 2-acetylthiophene oxime

In a 1 liter capacity four necked flask provided with a stirrer, a dropping funnel, a thermometer and a cooling tube were placed 100 g (0.794 mole) of 2-acetylthiophene, 59.8 g of hydroxylamine hydrochloride, 44.3 g of sodium carbonate, 192 g of methanol and 225 g of water, and the mixture was heated to the reflux temperature under stirring. Then acetic acid was added to the mixture to adjust it at a pH of 4, and refluxed under stirring for 2 hours.

Thereafter, a portion of methanol was distilled off from the reaction mixture, which was then cooled, and the resultant precipitates were filtered, washed with water, and dried, to provide 110.2 g (98.5% yield) of 2-acetylthiophene oxime as white crystals, a mixture of anti and syn forms, mp. 82°-93° C.

EXAMPLE 1

Synthesis of 2-(α-methoxyimino)ethylthiophene

In a 2 liter capacity four necked flask provided with a stirrer, a dropping funnel, a thermometer and a cooling tube were placed 141.7 g of N,N-dimethylformamide, 32.9 g (0.823 mole) of sodium hydroxide and 35.4 g of water.

A solution of 110.2 g (0.782 mole) of 2-acetylthiophene oxime in 104 g of N,N-dimethylformamide was added dropwise at 15°-20° C. into the flask over 1 hour under stirring, and the mixture was then cooled to 10° C., followed by the dropwise addition thereto of 110.0 g (0.864 mole) of 99% dimethylsulfuric acid at 10° C. over 1 hour. After the addition, the reaction mixture was stirred at 10° C. for another 30 minutes.

Thereafter the reaction mixture was diluted with water, extracted with chloroform, the extract was washed with water, and chloroform was distilled off from the extract. The residue was distilled in vacuo to provide 100.6 g of 2-(α-methoxyimino)ethylthiophene as colorless and transparent liquid, bp. 70°-72° C./3 mmHg. The yield was 83% based on 2-acetylthiophene oxime.

The elemental analysis data, spectral data and molecular weight determined by mass spectroscopy of 2-(α-methoxyimino)-ethylthiophene are as follows:

| Elemental Analysis: | | | | |
|---|---|---|---|---|
| | C | H | N | S |
| Observed: | 54.43 | 5.80 | 9.00 | 20.45 |
| Calculated: | 54.19 | 5.81 | 9.03 | 20.65 |

NMR (δ ppm, CDCl$_3$):
  2.18-2.30 (s. 3H), 3.92-4.00 (s. 3H), 6.90-7.49 (m. 3H).
IR (cm$^{-1}$):
  2960, 2945, 2900, 2825, 1440, 1305, 1240, 1060, 1040, 896, 855, 710.
Molecular Weight: 155

EXAMPLE 2

The reactions were carried out using alkylating agents, bases and solvents shown in Table 1 in the same amounts in Example 1, respectively, under otherwise the same reaction conditions as in Example 1, to provide 2-(α-alkoxyimino)ethylthiophenes as shown in Table 1.

The appearances, boiling points, elemental analysis data, spectral data and molecular weights determined by mass spectroscopy of 2-(α-ethoxyimino)ethylthiophene (No. 5), 2-(α-n-butoxyimino)ethylthiophene (No. 7), 2-(α-isopropoxyimino)-ethylthiophene (No. 9) and 2-(α-tert.-butoxyimino)ethylthiophene (No. 11) are as follows:

TABLE 1

| No.[1] | Solvents[2] | Bases | Alkylating Agents | Reaction Products (I) R | Yields (%) |
|---|---|---|---|---|---|
| 1 | $CH_3OH$ | $CH_3ONa$ | $CH_3I$ | $CH_3$ | 57 |
| 2 | $CH_3OH$ | $CH_3ONa$ | $(CH_3)_2SO_4$ | $CH_3$ | 63 |
| 3 | DMF | NaH | $(CH_3)_2SO_4$ | $CH_3$ | 94 |
| 4 | THF | NaH | $(CH_3)_2SO_4$ | $CH_3$ | 65 |
| 5 | $C_2H_5OH$ | $C_2H_5ONa$ | $C_2H_5I$ | $C_2H_5$ | 59 |
| 6 | 80% DMF | NaOH | $(C_2H_5)_2SO_4$ | $C_2H_5$ | 85 |
| 7 | $n-C_4H_9OH$ | $n-C_4H_9OK$ | $n-C_4H_9Br$ | $n-C_4H_9$ | 64 |
| 8 | 80% DMF | $(n-C_4H_9)_2SO_4$ | $(n-C_4H_9)_2SO_4$ | $n-C_4H_9$ | 86 |
| 9 | DMF | NaH | $iso-C_3H_7I$ | $iso-C_3H_7$ | 93 |
| 10 | 80% DMF | NaOH | $iso-C_3H_7I$ | $iso-C_3H_7$ | 78 |
| 11 | DMF | NaH | $t-C_4H_9I$ | $t-C_4H_9$ | 95 |

Notes:
[1]In Nos. 1, 2, 4, 5 and 7, after completion of the reaction, the reaction mixture was distilled, to provide the objective compounds.
[2]DMF: N,N-dimethylformamide; THF: tetrahydrofurane; 80% DMF: 80% aqueous solution of N,N-dimethylformamide

---

2-(α-ethoxyimino)ethylthiophene
Appearances: colorless and transparent liquid
Bp.: 77-78° C./2 mmHg

| Elemental Analysis: | | | | |
|---|---|---|---|---|
| | C | H | N | S |
| Observed: | 56.52 | 6.78 | 8.32 | 18.71 |
| Calculated: | 56.80 | 6.51 | 8.28 | 18.93 |

NMR (δ ppm, $CDCl_3$):
  1.2-1.5 (t. 3H), 2.18-2.29 (s. 3H), 4.05-4.40 (q, 2H), 6.85-7.45 (m. 3H).
IR ($cm^{-1}$):
  2980, 2940, 2880, 1595, 1442, 1380, 1300, 1230, 1095, 1050, 990, 921, 910, 890, 855, 705.
Molecular Weight: 169

---

2-(α-isoproxyimino)ethylthiophene
Appearances: colorless and transparent liquid
Bp.: 83-85° C./2 mmHg

| Elemental Analysis: | | | | |
|---|---|---|---|---|
| | C | H | N | S |
| Observed: | 59.28 | 7.02 | 7.92 | 17.24 |
| Calculated: | 59.02 | 7.10 | 7.65 | 17.49 |

NMR (δ ppm, $CDCl_3$):
  1.20-1.42 (d. 6H), 2.18-2.30 (s. 3H), 4.06-4.42 (s. 1H), 6.90-7.55 (m. 3H).
IR ($cm^{-1}$):
  2970, 2945, 2880, 1595, 1440, 1380, 1300, 1235, 1090, 1050, 990, 900, 870, 710.
Molecular Weight: 183

---

2-(α-n-butoxyimino)ethylthiophene
Appearances: colorless and transparent liquid
Bp.: 94-98° C./3.5 mmHg

| Elemental Analysis: | | | | |
|---|---|---|---|---|
| | C | H | N | S |
| Observed: | 60.68 | 7.50 | 7.31 | 16.50 |
| Calculated: | 60.91 | 7.61 | 7.11 | 16.24 |

NMR (δ ppm, $CDCl_3$):
  0.85-1.10 (t. 3H), 1.20-2.00 (m, 4H), 2.20-2.31 (s. 3H), 4.08-4.32 (t. 3H), 8.9-7.50 (m. 3H).
IR ($cm^{-1}$):
  2970, 2950, 2880, 1600, 1440, 1380, 1300, 1240, 1080, 1040, 1000, 920, 900, 860, 710.
Molecular Weight: 197

---

2-(α-tert-butoxyimino)ethylthiophene
Appearances: colorless and transparent liquid
Bp.: 88-92° C./3.5 mmHg

| Elemental Analysis: | | | | |
|---|---|---|---|---|
| | C | H | N | S |
| Observed: | 60.72 | 7.49 | 7.21 | 16.38 |
| Calculated: | 60.91 | 7.61 | 7.11 | 16.24 |

NMR (δ ppm, $CDCl_3$):
  1.20-1.45 (s. 9H), 2.20-2.30 (s. 3H), 6.90-7.48 (m. 3H).
IR ($cm^{-1}$):
  2975, 2950, 2885, 1590, 1440, 1390, 1295, 1240, 1060, 1040, 1000, 920, 910, 860, 720.
Molecular Weight: 197

EXAMPLE 3

Synthesis of 2-(α-methoxyimino)ethylthiophene

In a 2 liter capacity four necked flask provided with a stirrer, a dropping funnel, a thermometer and a cooling tube were placed 141.7 g of N,N-dimethylformamide and 83.0 g (0.822 mole) of triethylamine.

A solution of 110.2 g (0.782 mole) of 2-acetylthiophene oxime in 104 g of N,N-dimethylformamide was added dropwise at 15°-20° C. into the flask over 1 hour under stirring, and the mixture was then cooled to 10° C., followed by the dropwise addition thereto of 110.0 g (0.864 mole) of 99% dimethylsulfuric acid at 10° C. over 1 hour. After the addition, the reaction mixture was stirred at 10° C. for another 30 minutes.

Thereafter the reaction mixture was diluted with water, extracted with chloroform, the extract was washed with water, and chloroform was distilled off from the extract. The residue was distilled in vacuo to provide 75.2 g of 2-(α-methoxyimino)ethylthiophene as colorless and transparent liquid, bp. 70°-72° C./3 mmHg. The yield was 62% based on 2-acetylthiophene oxime.

EXAMPLE 4

Synthesis of 2-(α-methoxyimino)ethylthiophene

In a 200 ml capacity four necked flask provided with a stirrer, a dropping funnel, a thermometer and a cooling tube were placed 25.2 g (0.2 mole) of 2-acetylthiophene, 18.4 g (0.22 mole) of 0-methylhydroxylamine hydrochloride, 11.7 g of sodium carbonate, 20 g of methanol and 60 g of water. An amount of 2 g of acetic acid was added to the resultant mixture with stirring to adjust the pH of the mixture at 4.5, and the mixture was heated at the reflux temperatures for 2 hours.

After completion of the reaction, 40 g of water were added to the resultant reaction mixture and the mixture was cooled to room temperatures. The mixture was then extracted with chloroform, the extract was washed with water, and chloroform was distilled off from the extract. The residue was distilled in vacuo to provide 29.5 g of 2-(α-methoxyimino)-ethylthiophenene as colorless and transparent liquid, bp. 70°–72° C./3 mmHg. The yield was 95% based on 2-acetylthiophene.

EXAMPLE 5

The reactions were carried out using 0-alkylhydroxylamines, bases and solvents, and further, optionally acetic acid or propionic acid, as shown in Table 2 under otherwise the same reaction conditions as in Example 4, to provide 2-(α-alkoxyimino)ethylthiophenes as shown in Table 2.

EXAMPLE 6

Synthesis of 5-acetyl-2-(α-methoxyimino)ethylthiophene

In a 3 liter capacity four necked flask were placed 258 g (2.53 mole) of acetic anhydride, 61 g of polyphosphoric acid and 100.6 g (0.649 mole) of 2-(α-methoxyimino)ethylthiophene, and were reacted together at 100° C. for 9 hours under stirring. After completion of the reaction, the reaction mixture was left standing to room temperatures, and then excess amounts of acetic anhydride and polyphosphoric acid were diluted or decomposed with methanol and water. The resultant mixture was neutralized with a 20% by weight sodium hydroxide solution, and then was extracted with chloroform.

The chloroform extract was washed with water, and chloroform was distilled off therefrom, to provide 114.8 g of crude 5-acetyl-2-(α-methoxyimino)ethylthiophene, which upon recrystallization from methanol provided 67.1 g of purified 5-acetyl-2-(α-methoxyimino)ethylthiophene as pale yellow solids. The yield was 52.5% based on 2-(α-methoxyimino)ethylthiophene.

The melting point, elemental analysis data, spectral data and molecular weight determined by mass spectroscopy of 5-acetyl-2-(α-methoxyimino)ethylthiophene are as follows:

Mp.: 104–105° C.
Elemental Analysis:

|  | C | H | N | S |
|---|---|---|---|---|
| Observed: | 54.58 | 5.69 | 6.98 | 16.28 |
| Calculated: | 54.82 | 5.58 | 7.11 | 16.24 |

NMR (δ ppm, CDCl$_3$):
  2.20–2.33 (s. 3H), 2.53–2.56 (s. 3H), 3.98–4.06 (s. 3H), 7.17–7.65 (dd. 2H).
IR (cm$^{-1}$):
  3100, 2930, 2900, 2810, 1650, 1530, 1460, 1360, 1295, 1270, 1050, 920, 890, 590, 495.
Molecular Weight: 197

EXAMPLE 7

Synthesis of 5-(α-methoxyimino)ethyl-2-thiophenecarboxylic acid

In a 2 liter capacity four necked flask were placed 114.8 g of crude 5-acetyl-2-(α-methoxyimino)ethylthiophene (corresponding to 0.415 mole of 100% purified compound) and 116 g of methanol, and the mixture was heated to 70° C. under stirring. An amount of 1124 g of a 10% by weight aqueous sodium hypochlorite solution was added dropwise to the mixture at 10° C. over 30 minutes under stirring, and after the addition stirring was continued for further 30 minutes.

After completion of the reaction, the reaction mixture was left standing to room temperatures, washed with chloroform to remove therefrom unreacted 5-acetyl-2-(α-methoxyimino)ethylthiophene, made acidic with concentrated hydrochloric acid, and the resultant precipitates were separated by filtration, washed with water and dried, to provide 82.6 g of 5-(α-methoxyimino)ethyl-2-thiophenecarboxylic acid as white solids. The yield was 64.0% based on 2-(α-methoxyimino)ethylthiophene.

The melting point, elemental analysis data, spectral data and molecular weight determined by mass spectroscopy of 5-(α-methoxyimino)ethyl-2-thiophenecarboxylic acid are as follows:

Mp.: 205–206° C.
Elemental Analysis:

|  | C | H | N | S |
|---|---|---|---|---|
| Observed: | 48.42 | 4.43 | 7.21 | 15.92 |
| Calculated: | 48.24 | 4.52 | 7.04 | 16.08 |

NMR (δ ppm, CDCl$_3$):
  2.19–2.29 (s. 3H), 3.90–3.99 (s. 3H), 7.40–7.74 (dd. 2H).
IR (cm$^{-1}$):
  2950, 2825, 2675, 1700, 1670, 1542, 1480, 1430, 1310,

TABLE 2

| No. | Solvents | Bases | O-Hydroxylamine Salts | Reaction Conditions[1] | 2-(α-Alkoxyimino)ethylthiophenes | | |
|---|---|---|---|---|---|---|---|
|  |  |  |  |  | R in (I) | Bp. | Yields |
| 1 | CH$_3$OH/H$_2$O | Na$_2$CO$_3$ | NH$_2$OC$_2$H$_5$·HCl | Refluxed for 2 hrs. | C$_2$H$_5$ | 77–78° C./2 mmHg | 96 |
| 2 | DMF/H$_2$O | NaOH | NH$_2$OC$_2$H$_5$·HCl | 80–85° C. for 8 hrs. | C$_2$H$_5$ | 77–78° C./2 mmHg | 93 |
| 3 | CH$_3$OH/H$_2$O | Na$_2$CO$_3$ | NH$_2$O-i-Pr·HCl | Refluxed for 2.5 hrs. | i-Pr | 83–85° C./3 mmHg | 95 |
| 4 | DMF | NaH | NH$_2$O-i-Pr·HCl | 80–85° C. for 6 hrs. | i-Pr | 83–85° C./3 mmHg | 94 |
| 5 | CH$_3$OH/H$_2$O | Na$_2$CO$_3$ | NH$_2$O-n-Bu·H$_2$SO$_4$ | Refluxed for 3 hrs. | n-Bu | 94–98° C./3 mmHg | 96 |
| 6 | CH$_3$OH/H$_2$O | NaOH | NH$_2$O-t-Bu·H$_2$SO$_4$ | Refluxed for 3 hrs. | t-Bu | 88–92° C./3.5 mmHg | 94 |

Notes:
[1]In Nos. 1, 5 and 6, the reaction was carried out in the presence of acetic acid, and in No. 3 in the presence of propionic acid.
[2]Based on 2-acetylthiophene.

1280, 1060, 900, 830, 750, 530.
Molecular Weight: 199

EXAMPLE 8

The reactions were carried out using 2-(α-alkoxyimino)ethylthiophenes, acetylating agents, catalysts and solvents shown in Table 3 under otherwise the same reaction conditions as in Example 6, to provide 5-acetyl-2-(α-alkoxyimino)ethylthiophenes shown in Table 3.

Then these 5-acetyl-2-(α-alkoxyimino)ethylthiophenes were treated in the same manner as in Example 7, to provide corresponding 5-(α-alkoxyimino)ethyl-2-thiophenecarboxylic acids, respectively, as shown in Table 3.

The appearances, melting points, elemental analysis data, spectral data and molecular weights determined by mass spectroscopy of the 5-acetyl-2-(α-alkoxyimino)ethylthiophenes and 5-(α-alkoxyimino)ethyl-2-thiophenecarboxylic acids are shown below.

TABLE 3

| No. | R in (V) | Acetylating Agents | Catalysts[1] | Solvents | Reaction Conditions | Yields[2] (%) | Yields[3] (%) |
|---|---|---|---|---|---|---|---|
| 1 | CH$_3$ | (CH$_3$CO)$_2$O | H$_2$SO$_4$ | (CH$_3$CO)$_2$O | 100° C. × 1 hr | 41 | 49 |
| 2 | C$_2$H$_5$ | (CH$_3$CO)$_2$O | PPA | (CH$_3$CO)$_2$O | 100° C. × 10 hr | 52 | 63 |
| 3 | n-C$_4$H$_9$ | (CH$_3$CO)$_2$O | PPA | (CH$_3$CO)$_2$O | 100° C. × 20 hr | 55 | 51 |
| 4 | CH$_3$ | (CH$_3$CO)$_2$O | 85% PA | (CH$_3$CO)$_2$O | 100° C. × 10 hr | 48 | 59 |
| 5 | CH$_3$ | CH$_3$COCl | AlCl$_3$ | CHCl$_3$ | 50° C. × 3 hr | 43 | 53 |

Notes:
[1] Sulfuric acid, polyphosphoric acid (PAA) and 85% aqueous phosphoric acid (85% PA) were used in the same amount in weight as is Example 1. Acetyl chloride and aluminum chloride were used in amounts of 1.2 moles and 2.5 moles per mole of the reactant.
[2] Yields of 5-acetyl-2-(α-alkoxyimino)ethylthiophenes purified by recrystallization based on 2-(α-alkoxyimino)ethylthiophenes.
[3] Yields of 2-(α-alkoxyimino)ethyl-2-thiophenecarboxylic acids obtained by treating crude 5-acetyl-2-(α-alkoxyimino)ethylthiophenes in the same manner as in Example 2, which was obtained by acetylation of 5-acetyl-2-(α-alkoxyimino)ethylthiophenes.

---

5-acetyl-2-(α-ethoxyimino)ethylthiophene
Appearances: white solids
Mp.: 42–49° C.

Elemental Analysis:

|  | C | H | N | S |
|---|---|---|---|---|
| Observed: | 56.60 | 6.11 | 6.92 | 15.10 |
| Calculated: | 56.87 | 6.16 | 6.64 | 15.17 |

NMR (δ ppm, CDCl$_3$):
1.22–1.48 (t. 3H), 2.22–2.32 (s. 3H), 2.52–2.56 (s. 3H), 4.1–4.45 (q. 2H), 7.16–7.66 (dd. 2H).
IR (cm$^{-1}$):
2990, 2940, 1670, 1470, 1450, 1360, 1300, 1280, 1045, 1000, 935, 820, 600, 530.
Molecular Weight: 211

---

5-acetyl-2-(α-isoproxyimino)ethylthiophene
Appearances: white solids
Mp.: 64–69° C.

Elemental Analysis:

|  | C | H | N | S |
|---|---|---|---|---|
| Observed: | 58.82 | 6.56 | 6.01 | 14.50 |
| Calculated: | 58.67 | 6.67 | 6.22 | 14.22 |

NMR (δ ppm, CDCl$_3$):
1.25–1.50 (d. 6H), 2.20–2.30 (s. 3H), 2.52–2.56 (s. 3H), 4.00–4.56 (m. 1H), 7.16–7.66 (dd. 2H).
IR (cm$^{-1}$):
2995, 2940, 1650, 1530, 1465, 1380, 1290, 1050, 990, 950, 815, 595.
Molecular Weight: 225

---

5-(α-ethoxyimino)ethyl-2-thiophenecarboxylic acid
Appearances: white solids
Mp.: 150–164° C.

Elemental Analysis:

|  | C | H | N | S |
|---|---|---|---|---|
| Observed: | 50.92 | 5.08 | 6.39 | 15.22 |
| Calculated: | 50.70 | 5.16 | 6.57 | 15.02 |

NMR (δ ppm, CDCl$_3$):
1.16–1.38 (t. 3H), 2.20–2.29 (s. 3H), 4.03–4.35 (q. 2H), 7.35–7.72 (2H).
IR (cm$^{-1}$):
3125, 2990, 2680, 1700, 1540, 1480, 1425, 1345, 1310, 1280, 1120, 1000, 920, 846, 760, 505.
Molecular Weight: 213

---

5-(α-ethoxyimino)ethyl-2-thiophenecarboxylic acid
Appearances: white solids
Mp.: 136–148° C.

Elemental Analysis:

|  | C | H | N | S |
|---|---|---|---|---|
| Observed: | 52.79 | 5.61 | 6.32 | 14.01 |
| Calculated: | 52.86 | 5.73 | 6.17 | 14.10 |

NMR (δ ppm, CDCl$_3$):
1.20–1.43 (d. 6H), 2.18–2.27 (s. 3H), 3.92–4.50 (m. 1H), 7.34–7.71 (dd. 2H).
IR (cm$^{-1}$):
3015, 2980, 2720, 1705, 1550, 1480, 1430, 1345, 1310, 1280, 1120, 1000, 915, 840, 760.
Molecular Weight: 227

---

5-(α-n-butoxyimino)ethyl-2-thiphecarboxylic acid
Appearances: white solids
Mp.: 125–135° C.

Elemental Analysis:

|  | C | H | N | S |
|---|---|---|---|---|
| Observed: | 54.68 | 5.99 | 5.71 | 13.21 |
| Calculated: | 54.77 | 6.22 | 5.81 | 13.28 |

NMR (δ ppm, CDCl$_3$):
0.83–0.99 (t. 3H), 1.16–1.90 (m. 4H), 2.20–2.30 (s. 3H), 4.05–4.30 (t. 2H), 7.36–7.73 (dd. 2H).
IR (cm$^{-1}$):
2960, 2950, 2880, 1710, 1678, 1545, 1482, 1422, 1342, 1310, 1280, 1120, 1080, 1050, 1000, 925, 830, 755.
Molecular Weight: 241

EXAMPLE 9

Synthesis of 2,5-diacetylthiophene

In a 2 liter capacity four necked flask were placed 114.8 g of crude 5-acetyl-2-(α-methoxyimino)ethylthiophene (corresponding to 0.415 mole of 100% purified compound) and 424 g of concentrated hydrochloric acid, and the mixture was stirred at 70° C. under stirring for 8 hours to hydrolyze 5-acetyl-2-(α-methoxyimino)ethylthiophene.

After completion of the reaction, the reaction mixture was extracted with chloroform, the extract was washed with water, and chloroform was distilled off therefrom, to provide crude 2,5-diacetylthiophene, which was then washed with diethyl ether, to provide 60.0 g of purified 2,5-diacetylthiophene as pale yellow crystals, mp. 171°-173° C. (literature 172°-173° C.), in yields of 86% based on 5-acetyl-2-(α-methoxyimino)ethylthiophene. The yield based on 2-acetylthiophene was 45.0%.

The elemental analysis data, spectral data and molecular weight determined by mass spectroscopy of 2,5-diacetylthiophene obtained are shown below.

| Elemental Analysis: | C | H | S |
|---|---|---|---|
| Observed: | 57.40 | 4.70 | 18.97 |
| Calculated: | 57.14 | 4.76 | 19.05 |

NMR (δ ppm, CDCl$_3$):
2.62 (s. 6H), 7.98 (s. 2H).
Molecular Weight: 168

EXAMPLE 10

5-Acetyl-2-(α-alkoxyimino)ethylthiophenes listed in Table 4 were hydrolyzed with acids listed in Table 4 in the same manner as in Example 9, respectively, to provide 2,5-diacetylthiophene. The yields A of 2,5-diacetylthiophene based on 5-acetyl-2-(α-alkoxyimino)ethylthiophenes and the yields B based on 2-acetylthiophene are shown in Table 4.

TABLE 4

| R in Starting Materials (IV) | Acids Used | Yields A (%) | Yields B (%) |
|---|---|---|---|
| CH$_3$ | H$_2$SO$_4$ | 83 | 43 |
| C$_2$H$_5$ | HCl | 87 | 47 |
| n-Butyl | HCl | 86 | 45 |

EXAMPLE 11

Synthesis of 5-acetyl-2-thiophenecarboxylic acid

In a 2 liter capacity four necked flask were placed 82.6 g of 5-(α-methoxyimino)ethyl-2-thiophenecarboxylic acid, 390 g of water and 1015 g of concentrated hydrochloric acid, and the mixture was stirred at 55° C. under stirring for 6 hours to hydrolyze 5-(α-methoxyimino)ethyl-2-thiophenecarboxylic acid.

After completion of the reaction, the reaction mixture was left standing to room temperatures, and the resultant precipitates were filtered, washed with water, and dried, to provide 63.5 g of 5-acetyl-2-thiophenecarboxylic acid as white crystals, mp. 208°-210° C. (literature 203°-206° C.), in yields of 90.0% based on 5-(α-methoxyimino)ethyl-2-thiophenecarboxylic acid. The yield based on 2acetylthiophene was 47.1%.

The elemental analysis data, spectral data and molecular weight determined by mass spectroscopy of 5-acetyl-2-thiophenecarboxylic acid obtained are shown below.

| Elemental Analysis: | C | H | S |
|---|---|---|---|
| Observed: | 49.53 | 3.50 | 18.78 |
| Calculated: | 49.41 | 3.53 | 18.82 |

NMR (δ ppm, CDCl$_3$):
2.56 (s. 3H), 7.72-7.93 (d. 2H).
Molecular Weight: 170

EXAMPLE 12

5-(α-Alkoxyimino)ethyl-2-thiophenecarboxylic acids listed in Table 5 were hydrolyzed with acids listed in Table 5, respectively, in the same manner as in Example 11, to provide 5-acetyl-2-thiophenecarboxylic acid. The yields A of 5-acetyl-2-thiophenecarboxylic acid based on 5-(α-alkoxyimino)ethylthiophenecarboxylic acid and the yields B based on 2-acetylthiophene are shown in Table 5.

TABLE 5

| R in Starting Materials (V) | Acids Used | Yields A (%) | Yields B (%) |
|---|---|---|---|
| CH$_3$ | H$_2$SO$_4$ | 85 | 44 |
| C$_2$H$_5$ | HCl | 90 | 48 |
| n-Butyl | HCl | 90 | 44 |

EXAMPLE 13

Synthesis of 5-nitro-2-(α-methoxyimino)ethylthiophene

In a 1 liter capacity four necked flask provided with a reflux condensor, a thermometer and a stirrer were placed 200 g of acetic anhydride and 62 g (0.40 mole) of 2-(α-methoxyimino)ethylthiophene. To the resultant mixture were added dropwise over 1.5 hours acetyl nitrate which had been prepared by reacting 153.0 g (1.50 mole) of acetic anhydride with 53.6 g (0.8 mole) of 94% nitric acid at 5° C., and the resultant mixture was stirred for another 4 hours.

After completion of the reaction and cooling the mixture to 10° C., methanol and water were added to the reaction mixture to decompose excess amounts of acetic anhydride, and then the e reaction mixture was extracted with chloroform.

Chloroform was distilled off from the extract to provide a mixture of crude 5-nitro-2-(α-methoxyimino)ethylthiophene and 4-nitro-2-(α-methoxyimino)ethylthiophene in weight ratios of 9 to 1. The mixture was recrystallized from ethanol, to provide 60.0 g of 5-nitro-2-(α-methoxyimino)ethylthiophene as pale yellow solids in yields of 75% based on 2-(α-methoxyimino)ethylthiophene.

The melting point, elemental analysis data, spectral data and molecular weight determined by mass spectroscopy of 5-nitro-2-(α-methoxyimino)ethylthiophene are shown below.

Mp: 117-118°C.

| Elemental Analysis: | C | H | N | S |
|---|---|---|---|---|
| Observed: | 41.71 | 3.65 | 14.25 | 15.72 |
| Calculated: | 42.00 | 4.00 | 14.00 | 16.00 |

-continued

NMR (δ ppm, D₆-DMSO, TMS)
2.20 (s. 3H), 3.94 (s. 3H), 7.45–8.15 (dd. 2H).
Molecular Weight: 200

EXAMPLE 14

Synthesis of 5-nitro-2-acetylthiophene

In a 1 liter capacity four necked flask provided with a reflux condensor, a thermometer and a stirrer were placed 800 g of 25% aqueous hydrochloric acid solution and 60.0 g (0.3 mole) of 5-nitro-2-(α-methoxyimino)ethylthiophene, and the resultant mixture was stirred at 60° C. for 4 hours. After completion of the reaction and cooling the mixture to room temperatures, the reaction mixture was extracted with chloroform.

Chloroform was distilled off from the extract to provide 50.3 g (0.294 mole) of 5-nitro-2-acetylthiophene, mp. 108°–109° C., in yields of 98% based on 5-nitro-2-(α-methoxyimino)ethylthiophene.

EXAMPLE 15

Synthesis of 5-bromo-2-(α-methoxyimino)ethylthiophene

In a 500 ml capacity four necked flask provided with a reflux condensor, a thermometer and a stirrer were placed 300 ml of chloroform, 62.0 g (0.4 mole) of 2-(α-methoxyimino)ethylthiophene and 1.0 g of iron powder. To the resultant mixture were added dropwise at the reflux temperature 64 g (0.4 mole) of bromine over 4 hours, and then the mixture was stirred for another 4 hours at the reflux temperatures.

After completion of the reaction, chloroform was distilled off from the reaction mixture, and then the resultant precipitates were dissolved in methanol, and then the iron powders were separated from the resultant solution by filtration.

The concentration of the methanol solution provided 96.5 g of crude 5-bromo-2-(α-methoxyimino)ethylthiophene, which was recrystallized from isopropyl alcohol to provide 79.6 g (0.34 mole) of purified 5-bromo-2-(α-methoxyimino)ethylthiophene as whiye solids in yields of 85% based on 2-(α-methoxyimino)ethylthiophene.

The melting point, elemental analysis data, spectral data and molecular weight determined by mass spectroscopy of 5-bromo-2-(α-methoxyimino)ethylthiophene are shown below.

Mp: 70–71°C.
Elemental Analysis:

|  | C | H | N | S |
|---|---|---|---|---|
| Observed: | 36.12 | 3.27 | 5.94 | 13.81 |
| Calculated: | 35.90 | 3.42 | 5.98 | 13.68 |

NMR (δ ppm, D₆-DMSO, TMS)
2.15 (s. 3H), 3.86 (s. 3H), 7.16–7.29 (dd. 2H).
Molecular Weight: 234

EXAMPLE 16

Synthesis of 5-bromo-2-acetylthiophene

In a 1 liter capacity four necked flask provided with a reflux condensor, a thermometer and a stirrer were placed 906 g of 25% aqueous hydrochloric acid solution and 79.6 g (0.34 mole) of 5-bromo-2-(α-methoxyimino)ethylthiophene, and the resultant mixture was stirred at 60° C. for 3 hours. After completion of the reaction, the reaction mixture was cooled to 5° C., and the resultant precipitates were filtered to provide 66.2 g (0.323 mole) of 5-bromo-2-acetylthiophene, mp. 92°–93° C.

The yield based on 5-bromo-2-(α-methoxyimino)ethylthiophene was 95%.

EXAMPLE 17

Synthesis of 5-chloro-2-(α-methoxyimino)ethylthiophene

In a 500 ml capacity four necked flask provided with a reflux condensor, a thermometer and a stirrer were placed 300 ml of chloroform, 62.0 g (0.4 mole) of 2-(α-methoxyimino)ethylthiophene and 3.5 g of aluminum chloride. To the resultant mixture were added dropwise at room temperatures 61.2 g (0.44 mole) of surfuryl chloride, and then the mixture was stirred for another 5 hours at the reflux temperatures.

After completion of the reaction, the reaction mixture was added to water, and chloroform layer was separated, followed by concentration to provide 47.0 g (0.248 mole) of 5-chloro-2-(α-methoxyimino)ethylthiophene in yields of 62% based on 2-(α-methoxyimino)ethylthiophene.

The melting point, elemental analysis data, spectral data and molecular weight determined by mass spectroscopy of 5-chloro-2-(α-methoxyimino)ethylthiophene are shown below.

Mp: 32–34°C.
Elemental Analysis:

|  | C | H | N | S |
|---|---|---|---|---|
| Observed: | 44.11 | 4.41 | 7.17 | 16.80 |
| Calculated: | 44.33 | 4.22 | 7.39 | 16.89 |

NMR (δ ppm, D₆-DMSO, TMS)
2.21 (s. 3H), 3.92 (s. 3H), 7.10–7.33 (dd. 2H).
Molecular Weight: 189.5

EXAMPLE 18

Synthesis of 5-chloro-2-acetylthiophene

In a 1 liter capacity four necked flask provided with a reflux condensor, a thermometer and a stirrer were placed 906 g of 25% aqueous hydrochloric acid solution and 64.4 g (0.34 mole) of 5-chloro-2-(α-methoxyimino)ethylthiophene, and the resultant mixture was stirred at 60° C. for 3 hours.

After completion of the reaction, the reaction mixture was cooled to 5° C., and the resultant precipitates were filtered, to provide 52.4 g (0.326 mole) of 5-chloro-2-acetylthiophene, mp. 51°–52° C.

The yield based on 5-chloro-2-(α-methoxyimino)ethylthiophene was 96%.

EXAMPLE 19

Synthesis of 5-(α-methoxyimino)ethyl-2-thiophenesulfonic acid

In a 300 ml capacity four necked flask provided with a reflux condensor, a thermometer and a stirrer were placed 46.5 g (0.3 mole) of 2-(α-methoxyimino)ethylthiophene and 150 ml of 1,1,2,2-tetrachloroethane. To the resultant mixture were added dropwise 36.7 g (0.315 mole) of chlorosulfuric acid at room temperatures.

After stirring at 90° C. for 4 hours, the reaction mixture was cooled and the resultant precipitates were separated by filtration, to provide 65.2 g (0.277 mole) of 5-(α-methoxyimino)ethyl-2-thiophenesulfonic acid. This compound was unstable so that the melting point was not measured.

The elemental analysis data, spectral data and molecular weight determined by mass spectroscopy of 5-(α-methoxyimino)ethyl-2-thiophenesulfonic acid are shown below.

| Elemental Analysis: | | | | |
|---|---|---|---|---|
| | C | H | N | S |
| Observed: | 35.61 | 3.98 | 5.92 | 27.30 |
| Calculated: | 35.74 | 3.83 | 5.96 | 27.23 |

NMR (δ ppm, D$_6$-DMSO, TMS)
2.46 (s. 3H), 4.33 (s. 3H), 7.83–8.12 (dd. 2H).
Molecular Weight: 235

EXAMPLE 20

Synthesis of sodium 5-(α-methoxyimino)ethyl-2-thiophenesulfonate

In a 300 ml capacity four necked flask provided with a reflux condensor, a thermometer and a stirrer were placed 62.0 g (0.4 mole) of 2-(α-methoxyimino)ethylthiophene and were added thereto 140 g of 25% fuming sulfuric acid at 10° C. over 2 hours.

After the addition, the reaction mixture was added dropwise to water at 5° C. The resultant aqueous solution was neutralized with a 40% aqueous sodium hydroxide solution, the resultant sodium sulfate was filtered off, sodium chloride was added to the filtrate to salt out sodium 5-(α-methoxyimino)ethyl-2-thiophenesulfonate. The yield was 95.6 g (0.37 mole) and 93% based on 2-(α-methoxyimino)ethylthiophene.

The melting point, elemental analysis data and spectral data of sodium 5-(α-methoxyimino)ethyl-2-thiophene are shown below.

| Mp: more than 300°C. | | | | |
|---|---|---|---|---|
| Elemental Analysis: | | | | |
| | C | H | N | S |
| Observed: | 32.46 | 3.25 | 5.40 | 24.88 |
| Calculated: | 32.68 | 3.11 | 5.45 | 24.90 |

NMR (δ ppm, D$_6$-DMSO, TMS)
2.15 (s. 3H), 3.86 (s. 3H), 7.01–7.20 (dd. 2H).

EXAMPLE 21

Synthesis of sodium 5-acetyl-2-thiophenesulfonate

In a 2 liter capacity four necked flask provided with a reflux condensor, a thermometer and a stirrer were placed 95.6 g (0.37 mole) of sodium 5-(α-methoxyimino)ethyl-2-thiophenesulfonate and 987 g of a 25% aqueous hydrochloric acid solution, and the mixture was stirred at 60° C. for 1 hour.

After the completion of the reaction, the reaction mixture was cooled to room temperatures, adjusted to a pH of about 10 with a 40% aqueous sodium hydroxide solution, and then sodium chloride was added to the solution to salt out sodium 5-acetyl-2-thiophenesulfonate.

The yield was 80.9 g (0.355 mole) and 96% based on sodium 5-(α-methoxyimino)ethyl-2-thiophenesulfonate.

The melting point, elemental analysis data and spectral data of sodium 5-(α-methoxyimino)ethyl-2-thiophene sulfonate are shown below.

| Mp: more than 300°C. | | | |
|---|---|---|---|
| Elemental Analysis: | | | |
| | C | H | S |
| Observed: | 31.29 | 2.31 | 27.82 |
| Calculated: | 31.58 | 2.19 | 28.07 |

NMR (δ ppm, D$_6$-DMSO, TMS)
5.13 (s. 3H), 8.30–8.50 (dd. 2H).

What is claimed is:

1. A method of producing a 2,5-diacetylthiophene which comprises:
   acetylating a 2-(alpha-alkoxyimino)ethylthiophene having the general formula of

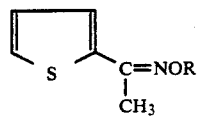

wherein R represents an alkyl having 1–4 carbons, with an acetylating agent, selected from the group consisting of acetic anhydride, acetyl chloride and acetyl bromide, in the presence of an acid catalyst selected from the group consisting of sulfuric acid, polyphosphoric acid, perchloric acid and aluminum chloride at a temperature of 40°–120° C., to provide a 5-acetyl-2-(alpha-alkoxyimino)-ethylthiophene; and then
   hydrolyzing the 5-acetyl-2-(alpha-alkoxyimino)ethylthiophene.

2. The method as claimed in claim 1 wherein R is methyl, ethyl, n-propyl, isopropyl, n-butyl, sec.-butyl or tert.-butyl.

3. The method as claimed in claim 1 wherein the acetylation is carried out using acetic anhydride as the acetylating agent in the presence of sulfuric acid, polyphosphoric acid or perchloric acid as the acid catalyst.

4. The method as claimed in claim 1 wherein the acetylation is carried out using acetyl chloride or acetyl bromide as the acetylating agent in the presence of aluminum chloride catalyst.

5. A method of producing a 5-acetyl-2-thiophenecarboxylic acid which comprises:
   acetylating a 2-(alpha-alkoxyimino)ethylthiophene having the general formula of

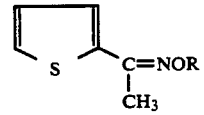

wherein R represents an alkyl having 1–4 carbons, with an acetylating agent, selected from the group consisting of acetic anhydride, acetyl chloride and acetyl bromide, in the presence of an acid catalyst selected from the group consisting of sulfuric acid, polyphosphoric acid, perchloric acid and aluminum chloride at a temperature of 40°–120° C., to provide a 5-acetyl-2-(alpha-alkoxyimino)-ethylthiophene;

reacting the 5-acetyl-2-(alpha-alkoxyimino) ethylthiophene with a hypohalite to provide a 5-(alpha-alkoxyimino)ethyl-2-thiophenecarboxylic acid; and then hydrolyzing the 5-(alpha-alkoxyimino)ethyl-2-thiophenecarboxylic acid.

6. The method as claimed in claim 5 wherein the hypohalite is an alkali metal or alkaline earth metal hypohalite.

7. The method as claimed in claim 6 wherein the alkali metal hypohalite is sodium hypohalite.

8. The method as claimed in claim 5 wherein R is methyl, ethyl, n-propyl, isopropyl, n-butyl, sec.-butyl or tert.-butyl.

9. The method as claimed in claim 5 wherein the acetylation is carried out using acetic anhydride as the acetylating agent in the presence of sulfuric acid, polyphosphoric acid or perchloric acid as the acid catalyst.

10. The method as claimed in claim 5 wherein the acetylation is carried out using acetyl chloride or acetyl bromide as the acetylating agent in the presence of aluminum chloride catalyst.

* * * * *